United States Patent
Tham et al.

[11] Patent Number: 5,957,129
[45] Date of Patent: Sep. 28, 1999

[54] ON-LINE FAULT DETECTION AND CORRECTION IN ANESTHESIA DELIVERY SYSTEM

[75] Inventors: Robert Q. Tham, Madison; Todd Keitel, DeForest, both of Wis.

[73] Assignee: Ohmeda Inc., Liberty Corner, N.J.

[21] Appl. No.: 08/902,886

[22] Filed: Jul. 30, 1997

[51] Int. Cl.⁶ .................................................. A61M 16/00
[52] U.S. Cl. .............................. 128/204.28; 128/205.24; 128/204.22
[58] Field of Search ........................ 128/204.28, 205.24, 128/204.18, 204.22, 203.12, 203.14, 204.26, 204.21

[56] References Cited

U.S. PATENT DOCUMENTS

| | | | |
|---|---|---|---|
| 5,094,235 | 3/1992 | Westenskow et al. | 128/204.22 |
| 5,296,706 | 3/1994 | Braig et al. . | |
| 5,315,989 | 5/1994 | Tobia | 128/204.28 |
| 5,386,833 | 2/1995 | Uhen . | |
| 5,632,270 | 5/1997 | O'Mohony et al. | 128/204.24 |
| 5,806,513 | 9/1998 | Tham et al. | 128/204.22 |

*Primary Examiner*—John G. Weiss
*Assistant Examiner*—Charles W. Anderson
*Attorney, Agent, or Firm*—Andrus, Sceales, Starke & Sawall

[57] ABSTRACT

An anesthesia delivery system having a means of determining the functioning of its gas mixer, vaporizer and analyzers, their accuracies and other characteristics by comparing, at high flow conditions, the input of oxygen concentration and agent concentration set by a clinician and delivered by the system, the input from a feedback respiratory analyzer of the inspired $O_2$ and agent concentrations and the input of a monitor analyzer that determines the $O_2$ and agent concentrations in the patient circuit. A CPU compares the three sets of input data to make various determinations since, at high flow conditions, all of the three sets of data should be consistent. Thus the CPU can determine from a comparison, whether one set of data is indicative of a faulty device, can provide a bias adjustment if an analyzer is merely off in its readings or carry out other safety and corrective functions based on comparing the three data inputs.

12 Claims, 1 Drawing Sheet

ON-LINE FAULT DETECTION AND CORRECTION IN ANESTHESIA DELIVERY SYSTEM

BACKGROUND

The present invention relates to medical anesthesia delivery systems for providing breathing gases and anesthesia to a patient. Specifically, the invention relates to a method and apparatus for operating a medical anesthesia machine and to an improved means of controlling the machine and determining faults in its operation.

Fundamentally, anesthesia machines are used during surgery by clinicians to deliver medical gases and inhaled anesthetic agent. Inspired breathing gases typically consist of a mixture of oxygen, nitrous oxide and other gases. The oxygen is supplemented to the patient to elevate the oxygen concentration above its concentration in air to provide a safe margin of inspired oxygen therapy. The anesthetic agent is added to the supply of breathing gases to provide the appropriate level of anesthesia so that the patient remains unconscious, sedated and relaxed during the surgical procedure. The inhaled anesthetic also provides amnesia of the surgical event.

It is common during the administration of anesthesia, for the patient to be connected to a partial rebreathing circuit, for example a circle breathing system. With such circuits, the patient's expired gases are recirculated, the $CO_2$ in the exhaled gases scrubbed, and the resulting gases are replenished with fresh gas and again administered to the patient during inspiration.

A common technique used in anesthesia today is referred to as low flow anesthesia where a minimal amount of fresh gas is added to the system. The technique enhances warming and humidification of the gases in the patient circuit since less colder and dry fresh gas is added and, of course, there is a savings in the cost of the anesthetic agent since that agent is recirculated rather that being vented from the system to a scavenging system or the like.

Generally, fresh gas flows in the range of 0.5 liters per minute can be used, although low flow may be up to around three liters per minute. Basically, the fresh gas flow is less than the patients minute volume so that there is partial rebreathing and the lower the fresh gas flow, the more rebreathing occurs. Due to the recirculation gases, however, the actual anesthetic concentration set by the user to be delivered by the vaporizer as well as the oxygen concentration is different than the inspired anesthetic and oxygen concentrations since the gases circulating in the patient circuit, in effect, dilute the concentrations of the agent and the oxygen delivered in the fresh gas stream.

High flow anesthesia, on the other hand, may be in the order of providing fresh gas into the system at the rate of three liters per minute and above and less gas is recirculated from the patient's exhalation back through the system. The fresh gas flow approximates or exceeds the patient's minute volume such that the exhaled gases are vented out of the system. Typical high flows without gas recirculation occurs above 1.1 times the patient's minute volume and, as indicated, result in a higher usage of anesthetic agent as well as a loss of heat and humidification in the patient circuit.

In the anesthesia machines generally in use today, the gas and vapor delivery is mechanically actuated by the clinician who adjusts the desired flow of oxygen out to a common gas outlet. At high flow rates, where most of the inspired concentrations to the patient are from the fresh gas, the ratio of the flow settings approximates the delivery of inspired gases. Thus, at these high flows, the clinician can manually set the various flow settings to obtain the concentrations of gas and vapor delivered to the patient. As indicated, however, the use of high flow rates is wasteful of anesthetic agent etc. as most of the agent laden gas is vented from the anesthesia machine.

The move to low flow anesthesia, while beneficial from an efficiency standpoint, is, however, tedious for the clinician to carry out manual adjustments of flow to achieve the targeted inspired concentration to the patient.

Accordingly, a new generation of anesthesia machines has emerged to facilitate very low to closed circuit anesthesia. Examples of these new low flow anesthesia machines are the Physioflex machine by Physio, Inc. and the machine described in U.S. Pat. No. 5,094,235 of Westenskow. With these newer machines, the user sets the oxygen concentration and either the inspired or expired anesthetic agent concentration to be delivered to the patient instead of setting fresh gas flow rate of agent vapor concentration delivered out of a common gas outlet. The machines use electronically controlled valves to blend the gas mixture and an electronically controlled vaporizer to deliver the anesthetic vapor. These electronic devices are controlled by a central processing unit to achieve the precise control needed at the low flows.

A patient respiratory gas monitor located at the common Y-piece of the breathing circuit senses and analyzes the oxygen concentration and the agent concentration in the inspired and expired gases to and/or from the patient. Another agent and oxygen monitor, collectively referred to as an inspiratory gas monitor, is used to monitor the agent and oxygen concentrations of gases in the inspired limb of the patient circuit and that measurement signal is fed to a CPU to close the control loops that actuate the electronic gas mixer and the electronic anesthetic vaporizer to achieve the clinician's desired delivery settings that are inputted to the CPU. The gas monitor in the Y-piece can thus check the feedback from the gas monitor used in the automatic control scheme and, preferably, the monitoring and feedback monitors are of differing technologies to avoid unrecognizable common mode failures.

Thus it would be advantageous to quickly and accurately determine when the monitoring and feedback monitors are malfunctioning totally or are simply out of calibration so that proper and prompt corrective action can be taken.

As with all monitors, their measurements drift and change with different environmental conditions. Differences in sensor technologies, location of measurements and processing technique further exacerbate any mismatch in the measurements of the same parameters. To overcome this, a bias correction can reduce the disagreement between these measurements. Furthermore, if the monitored data are consistent but different from the user set, it can be inferred that the delivery device failed to deliver the user set concentrations. Accordingly, it would be advantageous to be able to carry out that procedure automatically.

SUMMARY OF THE INVENTION

The present invention makes use of two sets of gas and agent monitors gas mixers and vaporizers to perform an on-line calibration of agent and oxygen monitors, compute the feedback control bias and isolate a failure in the subsystem. Accordingly, the aforesaid problems and difficulties with the present anesthesia machines have been alleviated by the present invention.

The invention consists of an electronically actuated anesthesia gas machine that is capable of delivering medical gases such as $O_2$, nitrous oxide and volatile anesthetic agent under the control of a central processing unit (CPU). Examples of such electronically controlled gas mixers are mass flow controllers commonly available in the process control industry. Several electronically actuated anesthetic vaporizers are commercially available such as the Engstrom Elsa, of Gambro Engstrom Company, Bromma, Sweden.

In carrying out the present invention, the patient may be ventilated by a ventilator such as the Model 7900 ventilator of Ohmeda Inc. or by means of a manual breathing bag manipulated by the clinician. As is common, the minute ventilation of the ventilation is monitored, that is, the flow to the patient over a period of one minute. The patient is connected to the ventilator and the fresh gas outlet by means of a circle type breathing circuit although other breathing circuits may be employed as well as various electronic gas mixers or electronic anesthetic vaporizers provided they can be remotely controlled by a CPU.

As previously described with the new generation anesthesia machines, the clinician can set the inspired oxygen concentration, the inspired or expired agent concentration and the fresh gas flow rate. The actual carrying out of attaining the set values rests with the CPU and its control of the various electronic gas mixing and agent vaporization functions. An oxygen analyzer, for example an $O_2$ fuel cell type and an agent analyzer, for example the Model RGM5250 of Ohmeda Inc. may be used to provide the feedback signal to the central processor unit to compare against the user set inspired concentration. These sensors are located at the inspiratory limb of the patient breathing circuit and will be collectively referred to as the inspiratory gas monitor. An alternate analyzer that can carry out the monitoring of both $O_2$ and agent concentrations in the patient circuit is the Rascal agent analyzer, also marketed by Ohmeda Inc. and based on Raman spectroscopy.

In carrying out the administration of anesthesia with such machine, in the control of the inspired oxygen or anesthetic agent, the difference between the measurement values and the user set values are used to adjust the delivery of the gas mixer and or electronic vaporizer to bring the inspired measured values to the concentrations set by the user and inputted to the CPU.

Algorithms to perform these automatic feedback controls are well understood and an example of such a control scheme is the PI control described in U.S. Pat. No. 5,094,235. The exact control strategy is not essential to this invention as long as the feedback values of measured $O_2$ and agent concentrations are used to adjust, if necessary, the electronic mixer and/or anesthetic vaporizer to match the values inputted by the clinician.

In closed circuit electronic gas delivery systems, the fresh gas flow rates are indirectly controlled such that adequate gas flows are delivered to maintain the breathing circuit volume and the gas and agent concentrations established by the clinician. The minimal flow delivery systems fresh gas flow rates are adjusted to minimize the gases that are exhausted from the breathing circuit.

As previously described, when the total fresh gas flow rate is low, more of the patient expired gases are returned through the absorber to be rebreathed by the patient. While this is desirable to save agent, the recirculated gases alter the composition of the fresh gas delivered to the patient. However, during high fresh gas flow rates, at open-circuit operations, excess gases are pushed through the absorber and relieved through the ventilator bellows. No patient gases are recirculated and therefore only the gases that are delivered by the electronic gas mixer and electronic agent vaporizer flow into the inspiratory limb of the patient circuit. The same concentrations of gases eventually also flow through the patient wye of the breathing circuit during the inspiratory phase of ventilation. Furthermore, once the dynamics of the high flow delivery settles, the composition of gases in the fresh gas lines and the inspiratory limb of the breathing circuit are the same. Therefore, the $O_2$ and agent concentrations set to and delivered by the gas mixer and vaporizer can be directly compared with the gas compositions measured at the inspired limb and the gases during the inspiratory phase of the gases measured at the patient wye by the respiratory gas monitor. This provides three sets of composition data relating to the same gases flowing through the system that can be compared to carry out various diagnoses and corrections to their inconsistencies.

The data with respect to composition at the three points can, therefore, at high flows, be compared for a number of purposes. One can compare the data between any of the corresponding parameters, i.e. $O_2$ concentration, and note the differences. If the data from two points compares favorable, that is, within certain error limits, and the third is outside a certain limit, then the device or monitor generating the errant data can be assumed to have failed and the clinician alerted to that potential problem. If all three data points agree within predetermined allowable limits, it can correspondingly be assumed that all of the monitors and mixers/vaporizers are operating normally. In such case, a bias value can be computed as the difference between the user monitored parameter and the feedback control parameter. The bias can be used to offset the feedback control error, thus matching the user set inspired gas delivery to the user monitored inspired measurement. That bias can remain even when the flow is returned to the low flow condition and can be readjusted (if desired) each time the flow is returned to a high flow delivery.

As a further use of the information available, if the two measurement data agree to within a certain tolerance, for example, the sum of their individual error tolerances, and a third (actuator) data differs from each of the first two data points by more than its known tolerance, for example, the error of each of the measurement tolerances but less than the combined tolerances, the sum of its measurement and each of the first two measurements, then the third parameter may be improved by recalibrating to the error tolerance weighted mean value of the first two data points. It also indicates that it is not a total failure but simply needs recalibration or adjustment.

Mathematically, lets assume that $X_1$ and $X_2$ are the readings of the first two measurements, respectively. Furthermore, assume that $e_1$ and $e_2$ are the known tolerances of the measurements $X_1$ and $X_2$, respectively.
If Magnitude of $|X_1-X_2|<|e_1|+|e_2|$ and Magnitude of $|e_1|<|X_{3-X1}|<|e_1|+|e_3|$ and Magnitude of $|e_2|<|X_{3-X2}|<|e_2|+|e_3|$ Then $X_{3,\ corrected}$ recalibration improvement to $X_3$ based on the error tolerance weighted mean value is as follows:

$$X_{3,corrected}=X_1*e_2/(e_1+e_2)+X_2*e_1/(e_1+e_2)$$

The above example by no means limit the method to compute the corrected recalibration values. Other correction methods established in the field of statistics can similarly be used to make the above correction.

In each of the foregoing data checks and recalibrations or adjustments, the need exists, obviously, to carry out the gathering of data from the three points during high flow. Such checks, therefore, may automatically be carried out during various times during the anesthesia that high flow is initiated such as when speed of response is needed to change a user set point or to rapidly refill the circuit gas volume following a disconnected circuit. If the clinically prompted increase in fresh gas flow does not occur for a long period, (the duration depends on the stability of the devices) the anesthesia machine can initiate such an increase in total fresh gas flow rate automatically at predetermined criteria, such as fixed intervals.

As can be seen, by increasing the fresh gas flow to high flow above the minute ventilation condition, the delivery device setting (derived from the clinician input) and the two pairs of gas measurements can be directly compared. In doing so, a failure in the gas delivery system can be localized. Furthermore, the performance of the gas delivery system can be retuned and therapy delivery can be matched to the clinician's monitored parameter.

Other features of the present anesthesia system will become more apparent in light of the following detailed description of a preferred embodiment thereof and as illustrated in the accompanying drawings.

BRIEF DESCRIPTION OF THE DRAWINGS

The FIGURE is a block diagram of an anesthesia system constructed in accordance with the present invention.

DETAILED DESCRIPTION OF THE INVENTION

Figure 1:
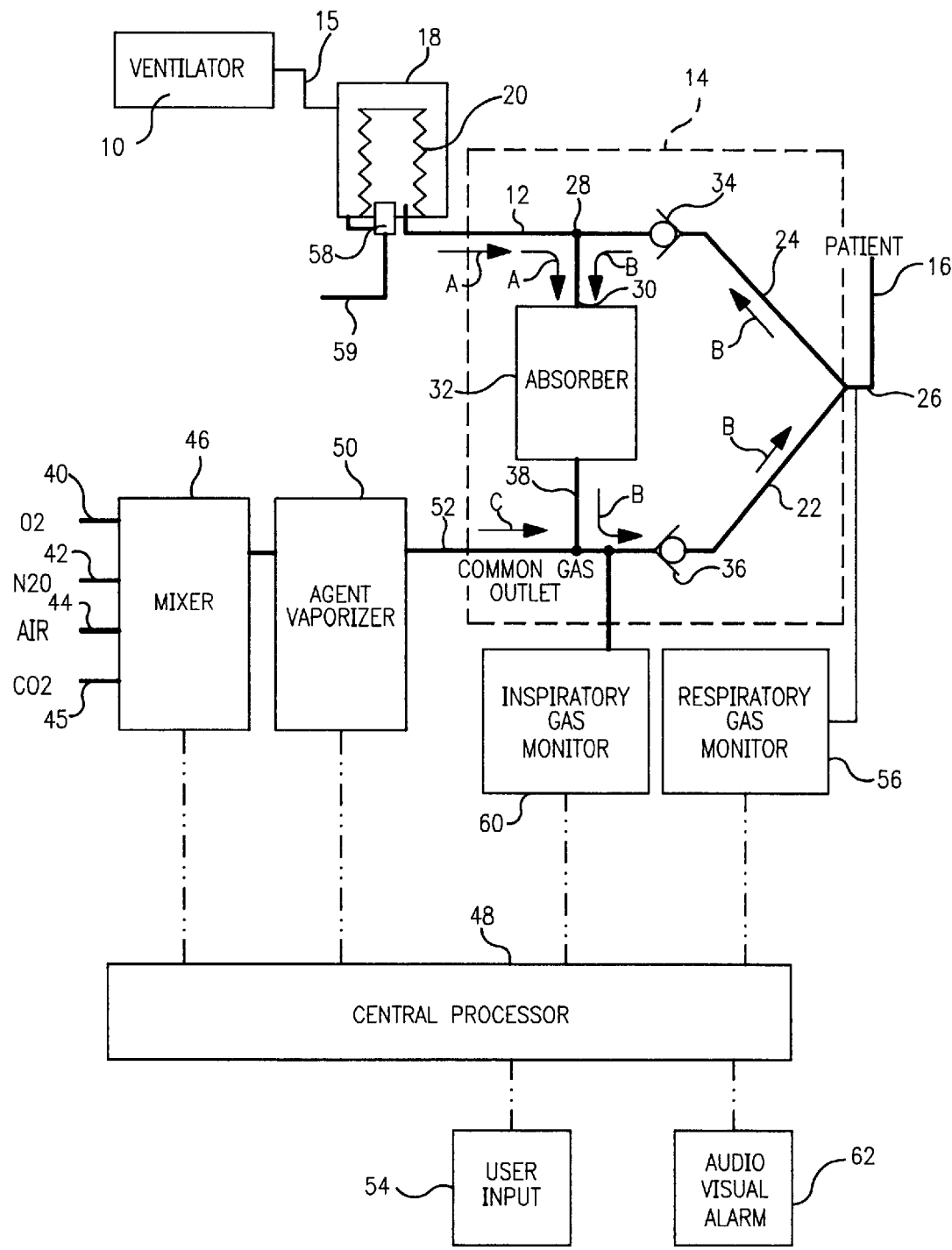

Referring now to the Figure, there is shown a block diagram of an anesthesia system adapted to carry out the subject invention. As shown, a ventilator 10 is provided and which may be of the type shown and described in U.S. Pat. No. 5,315,989 assigned to the present applicant and the disclosure of which is incorporated herein by reference. That ventilator 10 of the aforementioned U.S. Patent has an inhalation cycle and an exhalation cycle controlled by a central processing unit.

The ventilator 10 provides gas to the patient during the inhalation cycle via a conduit 12 to the patient breathing circuit 14 where it is delivered to the patient 16. The ventilator 10 typically includes a bellows assembly 18 and air or other powering gas is supplied to the bellows assembly 18 via conduit 15, exterior of the bellows 20 and which then collapses the bellows 20 to force gas within the bellows 20 to the patient 16. As will be described herein, the embodiment includes a ventilator 10 and bellows assembly 18, however, it will be understood that the present invention can be employed to the situation where the patient is being "bagged" by the clinician or is carrying out spontaneous breathing but is connected to the breathing circuit.

As also noted in the aforementioned U.S. Patent, the patient breathing circuit 14 itself conventionally includes an inspiratory limb 22 and an expiratory limb 24 and the patient is connected to a wye connection 26 located intermediate the inspiratory and the expiratory limbs 22,24. The means of connection may be an endotracheal tube, face mask or other interface between the patient 16 and the patient breathing circuit 14.

In conventional operation, gas is delivered to the patient 16 by means of a powering gas from ventilator 10 that collapses the bellows 20 to drive the gas into conduit 12 and then into the tee 28 where the gas enters a conduit 30 and passes through an absorber 32. After passing through the absorber 32, the gas enters the inspiratory limb 22 of the patient breathing circuit 14 to be administered to the patient 16. As the patient exhales, that exhalation, now laden with $CO_2$, passes through the expiratory limb 24 where it again passes through the tee 28 and continues to the absorber 32 where the $CO_2$ is eliminated by a $CO_2$ absorbing material, such as sodalime.

A pair of check valves 34 and 36 are positioned in the patient breathing circuit 14 in the expiratory and inspiratory limbs 24 and 22, respectively, to maintain the flow of gas in the proper direction around the circle patient breathing circuit 14.

A flow of fresh gas is also introduced into the patient breathing circuit 14 and, as shown, is added at a tee 38 and thus into the patient breathing circuit 14. That flow of fresh gas is provided from a source of gas, typically oxygen and nitrous oxide to aid in anesthetizing the patient. As shown in the Figure, there is a supply of oxygen 40, nitrous oxide 42, air 44 and carbon dioxide 45 and such supply may be through a central piping system of a hospital or may be through the use of individual cylinders of such gases.

In any event, the gases are mixed in a gas mixer 46 in the proportion desired by the user. The actual control of the proportions and the flow through the gas mixer 46 is controlled by a central processing unit (CPU) 48 as will be described. The mixed gas from the gas mixer 46 then passes through an agent vaporizer 50 where liquid anesthetic agent is vaporized and added to the stream of gas such that anesthetic laden gas continues into a conduit 52 and enters the patient breathing circuit 14 at the tee 38.

The control of the agent vaporizer 50 is by means of the CPU 48 and which determines the percentage concentration of anesthetic agent that is in the gas that enters the patient breathing circuit 14 and thus that is supplied to the patient 16 to induce and maintain anesthesia.

The CPU 48 is, in turn, controlled by a mixer setting device or user input 54 provided so that the clinician can input the data needed to determine the various parameters to provide the gas flow and anesthetic concentration desired to anesthetize the patient.

In the overall flow scheme of the present conventional system is therefore such that the gas in the bellows 20 is forced by the ventilator 10 into conduit 12 in accordance with the arrows A during the inhalation cycle of the patient 16. The gas thus passes through the tee 28 and through absorber 32 where it further passes through tee 38 and into the inspiratory limb 22 of the patient breathing circuit 14. At tee 38, fresh gas containing a predetermined concentration of an anesthetic agent is joined with the gas from the bellows 20 and proceeds with the gases already circulating in patient breathing circuit 14 and administered to the patient 16.

When the patient exhales, the exhaled gas passes through the expiratory limb 24 of the patient breathing circuit 14 through tee 28 and continue through the conduit 12 and into the bellows 20. At the same time, fresh gas that continuously flows into the circuit 14 from conduit 52 is also directed towards the bellows 20 after passing through the patient breathing circuit 14. When the bellows 20 reaches the end of its travel, any excess gas is popped off from the bellows 20 via pop-off valve 58 and exits the system via conduit 59.

During the inspiratory phase, the bellows 20 is driven downwardly by the ventilator 10. The unidirectional check valves 34 and 36 direct the gas from the bellows 20 to conduit 12 and through the absorber 32 where the gas is scrubbed of $CO_2$. Also directed is the fresh gas from conduit 52 towards the patient 16 via limb 22 of breathing circuit 14.

As can be seen, therefore, the anesthesia system is basically a circle system where the gas continues to pass in a circle as shown by the arrows B with the addition of fresh gas and the anesthetic agent added to that gas in the direction of Arrow C as the gas passes around the circle.

As a further component of the overall anesthesia system, an inspiratory gas monitor 60 is provided to detect certain gases entering into the inspiratory limb 22 and thus analyze the fresh gas added in conduit 52 carrying gas from the mixer 46 and to which an amount of anesthetic agent has been added by agent analyzer 50. A typical $O_2$ analyzer may be a oxygen fuel cell and an agent analyzer may be an RGM 5250 commercially marketed by Ohmeda Inc.

The $O_2$ and agent inspired measurements of the inspiratory gas monitor 60 are provided to CPU 48 to compute the rate of gas flows and anesthetic vapor delivered by the gas mixer 46 and vaporizer 50, respectively, to maintain the user delivered inspired concentration set by the input 54. The feedback control algorithm to meet the user desired setting is secondary to this invention.

A further monitor, a respiratory gas monitor 56 is also provided in the system and is located in the patient wye 26 and thus can monitor the actual gases that are either the inspired or expired gases of the patient 16. A typical analyzer for such user may be, again, the Ohmeda Inc. RGM analyzer or the Rascal gas analyzer, also commercially available from Ohmeda Inc. The inspiratory gas monitor 56 may also analyze the concentration of $CO_2$ and nitrous oxide that can reach the patient 16. That $CO_2$ and nitrous analysis is thus provided to the CPU 48.

An alarm 62 is also provided as controlled by the CPU 48, the purpose of which will be later explained.

As can now be seen, the overall anesthesia system is controlled by the CPU 48 based on feedback from the inspiratory gas monitor 60 in a feed back loop to achieve the agent and gas mixing concentrations set by the clinician with the user input 54 to CPU 48. The anesthesia system can thus operate at low flows since the overall control is CPU controlled and the clinician does not have to carry out the tedious titration of gases at the low flows. As also noted, at low flow, the concentrations are strongly influenced by the recirculation of the patients exhalation and therefore the composition of gases and vapor delivered out of the fresh gas line is different from the concentrations at the inspiratory gas monitor 60 and the respiratory gas monitor 56. However, at high flows greater than minute ventilation the composition of the fresh gas added to the system and analyzed by the inspiratory gas monitor 60 will be the same as the respiratory gas administered to the patient at the patient wye 26 and analyzed by the respiratory gas monitor 56.

As indicated, low flow is characteristic of a flow of about one liter per minute or less of fresh gas and, the lower the flow of fresh gas, certainly, the more rebreathing occurs in the system.

With high flow through the anesthesia system greater than the minute volume of the patient, say about 1.1 times, almost no rebreathing occurs. All of the exhaled gas is vented through the pop-off valve 58 and out through the conduit 59 which may be connected to a scavenging system to rid the surrounding atmosphere of the anesthetic laden gases. The minute ventilation is basically the amount of gas delivered to the patient in a minute and, in the aforedescribed case where a ventilator is used, the value of minute ventilation is normally provided as a setting on the ventilator or a reading from the ventilator control panel. The minute ventilation may, however, readily be determined from standard monitors in the cases where a ventilator is not used, such as when the clinician is actually ventilating the patient by manipulating a bag, i.e. bagging the patient, or where the patient is spontaneously breathing the gas through his own effort from the patient breathing circuit. In the case of the bagging situation or spontaneous breathing, the minute ventilation is readily determined by ascertaining the tidal volume, that is, the volume of gases inspired by the patient, and the breaths per minute. Such measurements are generally available to the clinician and thus, the minute ventilation is derived by multiplying the tidal volume in liters per breath by the breaths per minute to arrive at liters per minute.

Accordingly, the through flows, the gas compositions and vapor compositions through the patient breathing circuit 14 are the same and thus, both the inspiratory gas monitor 60 that is in the feedback loop to the CPU 48 and the respiratory gas monitor 56 should, during inspiration, read the same parameter values of gas composition and vapor concentration. Thus, two sets of measured data are available to the CPU 48 and should be consistent. There is also a set of data available from the user input 54 and, at high flows in the open circuit operations, are used to command the gas and agent composition in the fresh gas and therefore there are three sets of data that could bear some correlation, that is, if the system is operating correctly, the delivered gas and vapor concentration as set to the mixer and vaporizer should match the data of those compositions from the inspiratory gas monitor 60 as well as the inspired measurements of the respiratory gas monitor 56.

It should be noted that such correlation of the three sets of data will only occur at the high flows, therefore the system hereinafter described will be usable at start-up of the anesthesia system where a high flow is initiated, during the clinical operation where a high flow is initiated in order, for example, to make a rapid change in the gas or vapor concentrations, or upon depletion of the gas from the circuit and the machine is refilling the system or, alternatively the anesthesia system may periodically, on some predetermined timed cycle, simply switch into a high flow mode and carry out the system analysis and checks of the present invention.

Given the three sets of data, the CPU can now carry out various safety checks and analysis to detect and locate a fault and also to make certain corrections to the overall anesthesia system.

In one embodiment, the CPU, by a comparator, compares the various values of the oxygen concentration and the anesthetic vapor concentration that is set to the mixer and vaporizer, available from the inspiratory gas monitor 60 and the respiratory gas monitor 56 and compares the various sets of data. Thus, if all of the separate sets of data agree, it can be assumed that the system is operating properly. In such case, a bias value may be calculated by the CPU as a difference between the user monitored parameter and the feedback control parameter. The bias, so delivered, can be used to offset the feedback control error, thus better matching the user set inspired gas delivery to the user monitored inspired measurement. The bias, once determined, remains in the control algorithm even after the fresh gas is reduced back to low flow conditions.

If, on the other hand, two sets of data are within certain limits and the third set of data is outside a predetermined limit, it is assumed that the third set of data, either gas or agent delivered device, the respiratory gas monitor 56 or the inspiratory gas monitor 60 is in error and a error message or alarm can be activated in the alarm 62.

As a further use of the three sets of information available within the CPU 48, if the two measurement data agree to within a certain tolerance, for example, the sum of their individual error tolerances, and a third (actuator) data differs from each of the first two data points by more than a predefined tolerance, for example, the error of each of the measurements tolerances but less thant a combined tolerance, for example, the sum of its measurement and each of the first two measurements, then the third parameter may be improved by recalibrating to the error tolerance weighted mean value of the first two data points.

While the present invention has been set forth in terms of a specific embodiment, it will be understood that the anesthesia system herein disclosed may be modified or altered by the those skilled in the art to other configurations. Accordingly, the invention is to be broadly construed and limited only by the scope and spirit of the claims appended hereto.

We claim:

1. An anesthesia system for delivering a breathing gas containing a known anesthetic agent concentration to a patient, said anesthesia system comprising: a patient circuit for administering the breathing gas and anesthetic agent to the patient, said patient circuit having a wye connector for connection to a patient through which inhaled and exhaled gases pass to and from a patient, a fresh gas supply providing a fresh gas to said patient circuit, said fresh gas supply comprising an electronic controlled gas mixer for providing a mixture of gases at a settable proportion and an electronic controlled vaporizer for introducing anesthetic agent vapor to the mixture of gases from said electronic controlled gas mixer, a CPU controlling said electronic controlled vaporizer and said electronic controlled mixer, a mixer setting device operable by a user to input to said CPU the concentration of at least one component of the breathing gas desired to be administered to a patient through said patient circuit, a first gas monitor for analyzing said at least one component at or near said wye connector, a second gas monitor detecting the concentration of said at least one component in the gas circulating within said patient circuit, means to cause a high flow of fresh gas to enter said patient circuit from said fresh gas supply, and said CPU including means to compare the concentration of said at least one component determined by said first gas monitor, said second gas monitor and the concentration of said at least one component inputted by a user with said input device when said high flow of gas is entering said patient circuit.

2. An anesthesia system for delivering a breathing gas containing a known anesthetic agent concentration to a patient as defined in claim 1 wherein said at least one component is oxygen.

3. An anesthesia system for delivering a breathing gas containing a known anesthetic agent concentration to a patient as defined in claim 2 wherein said CPU determines a fault condition when the oxygen concentration determined from said first gas monitor, said second gas monitor and said oxygen concentration inputted by a user to said mixer setting device and delivered by the system are compared and are not within predetermined limits with respect to each other.

4. An anesthesia system for delivering a breathing gas containing a known anesthetic agent concentration to a patient as defined in claim 1 wherein said at least one component is anesthetic agent vapor.

5. An anesthesia system for delivering a breathing gas containing a known anesthetic agent concentration to a patient as defined in claim 3 wherein said CPU determines a fault condition when the anesthetic agent vapor concentration determined from said first gas monitor, said second gas monitor and said anesthetic agent concentration inputted by a user to said input device and delivered by the system are compared and are not within predetermined limits with respect each other.

6. An anesthesia system for delivering a breathing gas containing a known anesthetic agent concentration to a patient as defined in claim 1 wherein said means to cause a high flow of fresh gas to enter said patient circuit includes a timer that activates said means at predetermined intervals.

7. An anesthesia system for delivering a breathing gas containing a known anesthetic agent concentration to a patient as defined in claim 2 wherein said means to cause a high flow of gas to enter said patient circuit comprises a manual activator operable by a user.

8. An anesthesia system for delivering a breathing gas containing a settable anesthetic concentration to a patient as defined in claim 1 wherein said CPU provides a bias signal to correct the reading of at least one of said first and second gas monitors and said bias signal is determined by said CPU comparing said values of oxygen concentration from said first and second gas monitors.

9. An anesthesia system for delivering a breathing gas containing a known anesthetic agent concentration to a patient as defined in claim 1 wherein said system provides the breathing gas at a minute ventilation rate and said means to cause a high flow of fresh gas to enter said patient circuit comprises increasing the flow of said fresh gas to be greater than the minute volume.

10. Anesthesia system for delivering a breathing gas containing a known anesthetic agent concentration to a patient, said anesthesia system comprising: a patient circuit for administering the breathing gas and anesthetic agent to the patient, said patient circuit having a wye connector for connection to a patient through which inhaled and exhaled gases pass to and from a patient, a fresh gas supply providing a fresh gas to said patient circuit at a known rate, said fresh gas supply comprising an electronic controlled gas mixer for providing a mixture of gases at a known proportion and an electronic controlled vaporizer for introducing anesthetic agent vapor to the mixture of gases from said electronic controlled gas mixer, a CPU controlling said electronic controlled vaporizer and said electronic controlled mixer, a data input device operable by a user to input to said CPU the concentrations of oxygen and anesthetic agent desired to be administered to a patient through said patient circuit, a first gas monitor for analyzing oxygen and anesthetic agent at or near said wye connector, a second gas monitor detecting the concentration of oxygen and anesthetic agent in the gas circulating within said patient circuit, flow control means to increase the rate of flow of said fresh gas entering said patient circuit from said fresh gas supply, and said CPU including a comparator to compare the concentration of oxygen and anesthetic agent determined by said first gas monitor, said second gas monitor and the concentration of oxygen and anesthetic agent inputted by a user with said data input device when said increased flow of fresh gas is entering said patient circuit, said flow control means returning said rate of flow of said fresh gas entering said patient circuit from said fresh gas supply to said known rate when said comparator has completed comparing the oxygen and anesthetic agent concentrations.

11. An anesthesia system for delivering a breathing gas containing a known anesthetic concentration to a patient as defined in claim 10 wherein said first and second gas monitors are controlled by a bias signal from said CPU and said CPU further modifies said bias signal to one of said first and second gas monitors based on the comparison of said comparator.

12. An anesthesia system for delivering a breathing gas containing a known anesthetic concentration to a patient as defined in claim 10 wherein said comparator provides a signal when one of said first or second gas monitors or said fresh gas supply provides concentrations of oxygen and anesthetic agent outside a predetermined range with respect to the other two concentrations, said anesthesia system further including an alarm operable by said signal notifying the user as to which device providing such concentrations is outside said predetermined limit.

* * * * *

UNITED STATES PATENT AND TRADEMARK OFFICE
CERTIFICATE OF CORRECTION

PATENT NO. : 5,957,129
DATED : September 28, 1999
INVENTOR(S) : Tham et al.

It is certified that error appears in the above-indentified patent and that said Letters Patent is hereby corrected as shown below:

In the claims:

Claim 7, col. 10, line 12, after "of" insert ---fresh---; Claim 8, col. 10, line 15, delete "settable" and substitute therefor ---known---; Claim 8, col. 10, line 15, after "anaesthetic" insert ---agent---

Signed and Sealed this

Tenth Day of April, 2001

Attest:

NICHOLAS P. GODICI

*Attesting Officer*     *Acting Director of the United States Patent and Trademark Office*